United States Patent
Reiter et al.

(10) Patent No.: US 10,195,335 B2
(45) Date of Patent: *Feb. 5, 2019

(54) CHAMBER FOR BLOOD TREATMENT SYSTEM AND METHOD USING SAME

(71) Applicant: Fresenius Medical Care Deutschland GmbH, Bad Homburg v.d.H. (DE)

(72) Inventors: Reinhold Reiter, Crema (IT); Paolo Stabilini, Romanengo (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,468

(22) Filed: Feb. 23, 2018

(65) Prior Publication Data

US 2018/0177934 A1 Jun. 28, 2018

Related U.S. Application Data

(63) Continuation of application No. 13/331,063, filed on Dec. 20, 2011, now Pat. No. 9,931,455.

(Continued)

(30) Foreign Application Priority Data

Dec. 21, 2010 (EP) ..................................... 10015895

(51) Int. Cl.
*A61M 1/36* (2006.01)
(52) U.S. Cl.
CPC ................................ *A61M 1/3627* (2013.01)

(58) Field of Classification Search
CPC ..................... A61M 1/3627; A61M 2001/3632
(Continued)

(56) References Cited

U.S. PATENT DOCUMENTS

| | | |
|---|---|---|
| 4,559,034 A | 12/1985 | Kirita et al. |
| 4,765,959 A | 8/1988 | Fukasawa |

(Continued)

FOREIGN PATENT DOCUMENTS

| | | |
|---|---|---|
| DE | 34 20 278 A1 | 12/1985 |
| DE | 200 11 287 U1 | 3/2001 |

(Continued)

OTHER PUBLICATIONS

Oxford Dictionary, (http://www.oxforddictionaries.com/us/definition/american_english/form) accessed Aug. 28, 2015, 1 page.

*Primary Examiner* — Patrick J Orme
(74) *Attorney, Agent, or Firm* — Kilyk & Bowersox, P.L.L.C.

(57) ABSTRACT

A chamber is provided for a blood treatment system and has at least one space defined by a chamber wall, at least one blood inlet, and at least one inlet for a further fluid, which are connected with the space. Both the at least one blood inlet and the at least one inlet for the further fluid are formed on tube sections that protrude into the space of the chamber. In the operating condition of the chamber the space of the chamber is at least partly filled with blood or with a mixture of blood and either the further fluid or some other fluid. At least one, or preferably both, of the tube sections have a length such that the blood inlet and/or the inlet for the further fluid are located below the blood or fluid level in the chamber.

16 Claims, 2 Drawing Sheets

Related U.S. Application Data

(60) Provisional application No. 61/425,409, filed on Dec. 21, 2010.

(58) Field of Classification Search
USPC .......................... 206/486; 53/473; 604/6.15
See application file for complete search history.

(56) References Cited

U.S. PATENT DOCUMENTS

| | | | |
|---|---|---|---|
| 5,578,070 A | 11/1996 | Utterberg | |
| 5,830,185 A * | 11/1998 | Block, Jr. | ........... A61M 1/3627 604/122 |
| 6,908,446 B2 | 6/2005 | Yokoyama et al. | |
| 9,931,455 B2 * | 4/2018 | Reiter | ................. A61M 1/3627 |
| 2009/0107335 A1 | 4/2009 | Wilt et al. | |

FOREIGN PATENT DOCUMENTS

| | | | |
|---|---|---|---|
| EP | 0 062 913 A1 | 10/1982 | |
| EP | 1 210 956 A2 | 6/2002 | |
| EP | 2 186 533 A1 | 5/2010 | |
| EP | 2186533 A1 * | 5/2010 | .......... A61M 1/3627 |
| JP | S52-096360 U | 8/1977 | |
| JP | S58-10062 A | 1/1983 | |
| JP | S61-247468 A | 11/1986 | |

* cited by examiner

CHAMBER FOR BLOOD TREATMENT SYSTEM AND METHOD USING SAME

CROSS REFERENCE TO RELATED APPLICATIONS

This application is a Continuation of U.S. patent application Ser. No. 13/331,063, filed Dec. 20, 2011, now allowed, which in-turn claims the benefit of U.S. Provisional Application No. 61/425,409 filed Dec. 21, 2010, and claims priority to European Patent Application No. 10 015 895.5 filed Dec. 21, 2010, all of which are incorporated herein in their entireties by reference.

FIELD OF THE INVENTION

The present invention relates to a chamber for a blood treatment system with at least one space defined by a chamber wall as well as with at least one blood inlet and with at least one inlet for a further fluid, which are connected with the space.

BACKGROUND OF THE INVENTION

From the prior art it is known to provide a venous drip chamber downstream of the dialyzer of a dialysis machine, which is part of the extracorporeal blood circuit. The function of this venous drip chamber is to ensure a rather bubble-free reinfusion of the patient blood purified in the dialyzer to the patient.

From the prior art it is furthermore known to introduce an infusion solution, such as purified dialysate or a salt solution, into such drip chamber. Such supply can be effected in connection with the so-called pre-dilution before the dialyzer and/or in connection with the so-called post-dilution after the dialyzer.

FIG. 4 shows an embodiment known from the prior art in the form of a lid or headpiece of such venous drip chamber, on which a supply port 100 is arranged for the blood purified in the dialyzer.

Reference numeral 200 designates a supply port for said infusion solution.

As can furthermore be taken from FIG. 4, it is known to introduce the blood into the chamber by means of a tube section 30, wherein the tube section 30 includes an inlet 10 through which the blood is introduced into the chamber, as is indicated by the arrow in FIG. 4.

Said infusion solution is introduced by means of the supply port 200, wherein the inlet for the infusion solution is located above the fluid or blood level in the chamber, which is designated with the reference numeral 50. The infusion fluid drips or flows, as marked by the arrow in FIG. 4, onto the surface of the blood or the mixture of blood and the infusion solution.

Such configuration of a drip chamber has the disadvantage that due to the impingement of the infusion solution onto the surface of the fluid or blood present in the chamber the formation of microbubbles may occur, which can lead to an alarm condition being triggered and possibly the treatment being stopped.

SUMMARY OF THE INVENTION

Thus, it is the object underlying the present invention to develop a chamber as mentioned above to the effect that the formation of microbubbles in the drip chamber is largely or completely prevented.

Accordingly, it is provided that both the at least one blood inlet and the at least one inlet for the further fluid, such as an infusion solution, are formed on tube sections which protrude into the space of the chamber. In contrast to the configuration according to the prior art as shown in FIG. 4 it thus is provided that the inlet for the infusion fluid and/or for the further fluid is formed on a tube section which protrudes into the space of the chamber in which the blood or the mixture of blood and the infusion solution is contained.

In accordance with the present invention it is furthermore provided that the space of the chamber is at least partly filled with blood or with a mixture of blood and a further fluid or with some other fluid and that at least one of the tube sections has a length such that the blood inlet and/or the inlet for the further fluid are located below the blood or fluid level in the chamber. In this way it is ensured that at least in the operating condition of the chamber no dripping, not even from a small height, onto the surface of the blood present in the chamber or onto the surface of the mixture of blood and infusion solution or other fluid present in the chamber does occur. In accordance with a preferred aspect of the present invention, the blood and also the further fluid rather is introduced below the level of the blood or of the fluid present in the chamber. In this aspect the present invention thus relates to a chamber for a blood treatment system, whose space is at least partly filled with blood or with a mixture of blood and a further fluid or with some other fluid, wherein at least one of the tube sections has a length such that the blood inlet and/or the inlet for the further fluid are located below the fluid level or the blood level in the space of the chamber.

In this way, it is possible to avoid dripping of the further fluid onto the surface of the fluid or blood already present in the chamber and hence reduce the probability for the formation of microbubbles.

The term "tube section" should be interpreted broadly and comprises both rigid and elastic elements which are suitable to pass blood or the further fluid into the chamber. Thus, for example solid, e.g. plastic, tube sections, hoses etc. are taken into consideration.

The diameter as well as the dimensions and the shape of these tube sections can largely be chosen as desired. For example, their inside and outside diameter can be circular. However, configurations different therefrom are also comprised by the present invention. Furthermore, the present invention is not limited to the presence of exactly two tube sections. There can also be provided more than two tube sections, so that the blood for example is introduced into the chamber through more than one tube section and/or the further fluid is introduced through more than one tube section.

It is conceivable that at least one of the tube sections is arranged such that in the operating condition of the chamber it extends vertically or at an acute angle to the vertical. It thus is conceivable that two or more tube sections are provided, which are arranged substantially vertical and one of which includes one or more inlets for the blood and/or the other one of which includes one or more inlets for the further fluid.

The two tube sections can extend parallel or substantially parallel to each other. However, an angular arrangement of the tube sections relative to each other also is conceivable.

In a further aspect of the present invention it is provided that in the operating condition of the chamber the space of the chamber is partly filled with blood or with a mixture of blood and the at least one fluid or some other fluid and that above the blood or fluid level an air cushion is disposed.

Furthermore, it can be provided that the tube sections have a different length or the same length.

It is conceivable, for example, to design the tube section which carries the one or more inlets for the further fluid as long as or shorter or longer than the tube section which carries the one or more blood inlets.

It is particularly advantageous when the length of both tube sections is such that the inlets for the blood and the further fluid are located below the fluid level in the chamber.

In a further aspect of the present invention at least one of the tube sections includes one or more blood inlets or one or more inlets for the further fluid. Thus, the present invention is not limited to the fact that each tube section only has exactly one inlet, but also comprises the case that two or more than two inlets are provided per tube section.

In a further aspect of the present invention it is provided that the blood inlet and/or the inlet for the further fluid is arranged in the end region of the tube section, which protrudes into the chamber.

Furthermore, it can be provided that at least one of the tube sections includes a shell surface and an end surface protruding into the space of the chamber and that the at least one blood inlet and/or the at least one inlet for the further fluid is at least partly or also completely arranged in the shell surface. Due to this aspect of the present invention, a lateral introduction of the blood or further fluid, i.e. an introduction from the side, is conceivable. In this aspect, the blood and/or the further fluid thus is not introduced in a direction which coincides with the longitudinal axis of the tube section, but in a direction that extends at an angle thereto. It is conceivable that this angle lies in the range between 30° and 150°, preferably in a range between 60° and 120°, and particularly preferably in a range between 80° and 100° relative to the longitudinal axis of the tube section. If the angle is about 90°, for example, the blood thus flows first through the interior of the tube section and then at right angles thereto out of the tube section through the inlet into the chamber.

In a further aspect of the present invention it is provided that at least one of the tube sections includes a plurality of blood inlets or a plurality of inlets for the further fluid. This plurality of inlets can be arranged such that the blood flows from the tube section into the chamber in different directions. The same can apply to said further fluid. It is conceivable that the two inlets are arranged such that the blood or the further fluid flows out of the tube sections on opposite sides, so that opposite flow directions are obtained.

It is furthermore conceivable that the plurality of inlets are arranged at the same level, i.e. in the case of vertical tube sections at the same vertical position of the tube sections, and/or that the plurality of inlets have an identical size or also different sizes.

Furthermore, it can be provided that at least one of the tube sections has a wall in its end region protruding into the space of the chamber and that the at least one inlet is located adjacent to this wall. Thus, this wall can form the end of the tube section protruding into the space. Adjacent to this wall one or more inlets for the blood or for the further fluid can be located.

As an alternative to the above described embodiment with two inlets per tube section it is of course also conceivable to form more than two inlets, for example three or four inlets per tube section.

These inlets can be uniformly spaced in circumferential direction around the respective tube section. A non-uniform distribution also is conceivable.

Said introduction of the blood or of the further fluid by means of a plurality of inlets spaced from each other in circumferential direction involves the advantage that a vortex formation inside the chamber is effectively counteracted, which in turn involves the advantage that the occurrence of microbubbles is largely or completely prevented.

The one or more inlets for the blood or the one or more inlets for the further fluid can be arranged such that the blood or the further fluid is introduced in radial direction of the chamber or directed towards the chamber wall or also in tangential direction of the chamber or in circumferential direction or also in a direction between these two directions.

Furthermore, it can be provided that the tube sections are spaced from each other, so that separate inlets for blood on the one hand and for the further fluid on the other hand are present.

Furthermore, it can be provided that the chamber includes a base body and a lid or headpiece closing the base body and that the tube sections are arranged on the lid or headpiece and preferably extend through the lid or headpiece. The lid or headpiece can be firmly connected with the base body or also be releasable from the base body. In the case of a fixed design it is conceivable to design the base body and the lid or headpiece in one piece.

The present invention furthermore relates to the use of a chamber in a blood treatment system. Preferably the chamber is used as a venous chamber which is arranged downstream of a dialyzer.

In the operating condition of the chamber the space of the chamber can at least partly be filled with blood or with a mixture of blood and the further fluid or some other fluid and at least one of the tube sections can have a length such that the blood inlet and/or the inlet for the further fluid is located below the blood or fluid level in the chamber. As already explained above, the particularly preferred aspect of the present invention can be realized in that dripping of both the blood and the further fluid onto the surface of the blood present in the chamber or onto the surface of the fluid present in the chamber is prevented.

In a further aspect of the present invention it is provided that in the operating condition of the chamber the space of the chamber is partly filled with blood or with a mixture of blood and the further fluid or some other fluid and that above the blood an air cushion is disposed.

Furthermore, it can be provided that in the operating condition of the chamber at least one of the tube sections extends vertically or at an acute angle to the vertical.

As already explained above, it is advantageous when the one or more inlets for the blood and/or for the further fluid are formed on the tube section such that the blood and/or the further fluid exits from the tube section at an angle to the longitudinal axis of the tube section. This angle can lie for example in the range between 30° and 150°, preferably in a range between 60° and 120°, and particularly preferably in a range between 80° and 100°.

At least one of the tube sections can have a plurality of inlets which are arranged on the tube section such that the blood and/or the further fluid is discharged from the respective tube section in at least two different directions. In this way, too, the formation of vortices in the chamber and hence also the occurrence of microbubbles can largely or completely be prevented.

The further fluid can be an infusion solution, in particular a dialysis solution or a salt solution, such as a sodium chloride solution. The same is mixed with blood in the space of the chamber and then this mixture is supplied to the patient.

The present invention furthermore relates to a blood tubing system with at least one chamber. It can be provided that the blood tubing system is provided with a pre-dilution port and/or with a post-dilution port and that one or both of these ports are in fluid connection with the tube section for the further fluid or are connectable to form a fluid connection.

The present invention furthermore relates to a blood treatment system with at least one chamber or with at least one blood tubing system.

In an advantageous aspect of the present invention it is provided that the blood treatment system is a dialysis machine. The dialysis machine can be configured to perform a hemodialysis, a hemofiltration or also a hemodiafiltration with said machine.

Furthermore, it can be provided that the further fluid is provided by the dialysis machine.

BRIEF DESCRIPTION OF THE DRAWINGS

Further details and advantages of the present invention will be explained in detail with reference to an embodiment illustrated in the drawing, in which.

DETAILED DESCRIPTION OF THE DRAWINGS

Figure 1:
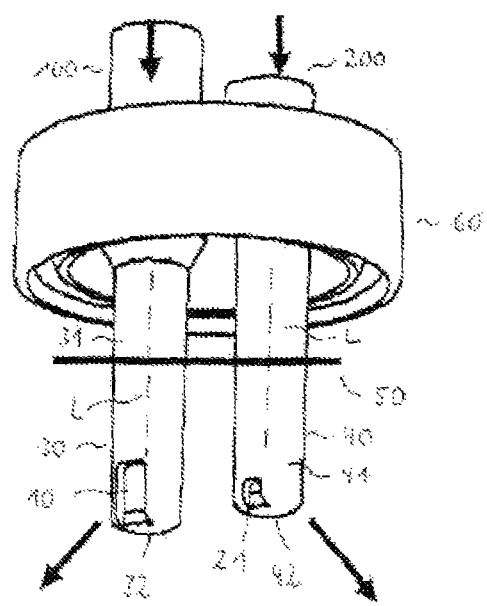
FIG. 1 shows a perspective representation of a lid of a chamber of the present invention in a view obliquely from below.

In a perspective view obliquely from below, FIG. 1 shows a head or lid region 60 of a venous chamber of an extracorporeal blood circuit of a dialysis machine.

Reference numeral 100 designates the supply port for the blood, and reference numeral 200 designates the supply port for the infusion solution. The supply port 100 is connected with the extracorporeal blood circuit. Through the supply port 100, the blood purified in the dialyzer flows into the venous chamber of the present invention, whose lid or headpiece 60 is shown in FIG. 1.

The supply port 200 for the infusion solution is connected with a suitable source for the infusion solution, such as dialysate, a sodium chloride solution, etc. Through this port 200, the infusion solution is supplied to the chamber. In the illustrated embodiment, this supply takes place downstream of the dialyzer, so that there is a post-dilution.

In principle, however, the present invention is not limited thereto, but provides for using a chamber also in the region of the pre-dilution.

In FIG. 1, reference numeral 50 designates the blood level or the level of the fluid present in the chamber. This fluid consists either of blood only or of a mixture of blood and said infusion fluid or of some other fluid. As can furthermore be taken from FIG. 1, the supply port 100 preferably is firmly or integrally connected with the tube section 30, and the supply port 200 preferably is firmly or integrally connected with the tube section 40 extending parallel thereto. Both tube sections 30, 40 are spaced from each other, as can be taken from FIG. 1. The supply ports 100, 200 can be an integral part of the tube sections 30, 40 or be connected with the same in a suitable way. It is also conceivable that the tube sections 30, 40 and/or the supply ports 100, 200 are integral parts of the lid or of the headpiece 60 of the chamber or are connected with the same in some other way, for example inserted into the same.

Reference numeral L designates the longitudinal axes of the two tube sections 30, 40 which protrude into the space of the chamber which on the head side is closed off by the headpiece 60 or by the lid 60.

As can furthermore be taken from FIG. 1, each of the tube sections 30, 40 includes an inlet 10, 21 in its shell surface 31, 41, through which blood on the one hand and the infusion fluid on the other hand gets into the fluid or blood already present in the chamber.

FIG. 1, furthermore, shows that both the inlet 10 for the blood and the inlet 21 for the further solution or for the infusion fluid is located below the level 50 of the fluid or blood already present in the chamber. FIG. 1 furthermore shows that the inlets 10, 21 are not arranged in the downwardly pointing end region 32, 42 of the tube sections 30, 40, but are arranged at least also or exclusively laterally, so that the blood or the further fluid exits from the tube sections 30, 40 laterally or at least also in a lateral direction.

In accordance with the present embodiment it is thus provided that both the inlet for the infusion solution and the inlet for the blood is located below the level 50 of the blood already present in the chamber or of the mixture of blood and infusion solution or some other fluid.

Furthermore, it is provided in accordance with the present embodiment that separate inlets for blood on the one hand and for the further solution on the other hand are present.

As can furthermore be taken from FIG. 1, the tube section 40 which carries the inlet for the further solution is formed slightly shorter than the tube section 30 which carries the inlet 10 for the blood. In principle it is also conceivable to design these two tube sections 30, 40 of identical length or to provide the height or position of the respective inlets 10, 21 at the same level or to design the tube section 40 longer than the tube section 30.

Figure 2:
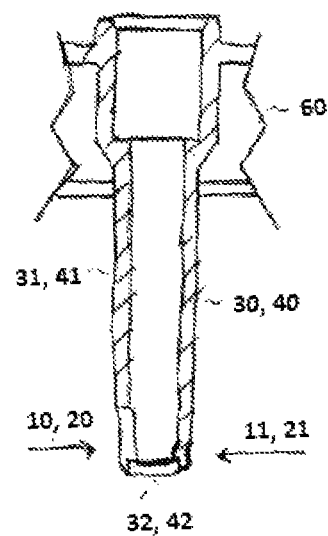
FIG. 2 shows a sectional representation through a tube section with inlets for blood or the further fluid.

FIG. 2 shows a sectional representation through the tube section 30 or also through the tube section 40. As can be taken from FIG. 2, the tube section 30, 40 is an integral part of the lid and preferably formed integrally with the same. Thus, an integrated infusion port can be realized by the present invention.

From FIG. 2 it can furthermore be taken that both the tube section 30 for supplying blood and the tube section 40 for supplying the further fluid is each formed with two inlets 10, 11, 20, 21 which directly adjoin the end-side wall 32, 42. As can also be taken from FIG. 3, these inlets are arranged opposite each other, which results in that the blood or the further solution exits from the respective tube section 30, 40 on opposite sides and enters the fluid already present in the chamber. This can be taken for example from FIG. 3. Here, reference numeral 30 designates the tube section for supplying blood, and reference numerals 10, 11 designate the inlets for blood. These inlets are arranged at the side of the tube section 30, i.e. laterally and in an opposed manner, which results in that, as shown in FIG. 3, the blood is discharged from the tube section 30 in opposed, i.e. in opposite directions.

This applies to the formation of the tube section 40 for supplying the further fluid. Here as well two opposed inlets 20, 21 are provided, which likewise have a different size. As shown in FIG. 3, the flow directions of the blood and of the further fluid are parallel when flowing out of the tube sections 30 and 40. However, a non-parallel outflow of blood on the one hand and of the further solution on the other hand also is comprised by the present invention.

In principle, the present invention also comprises the case that the respective inlets 10, 11 and 20, 21 are designed with an identical size. The inlets 10, 11 and 20, 21 can be arranged on the tube section at an identical level or also at different levels.

Figure 3:
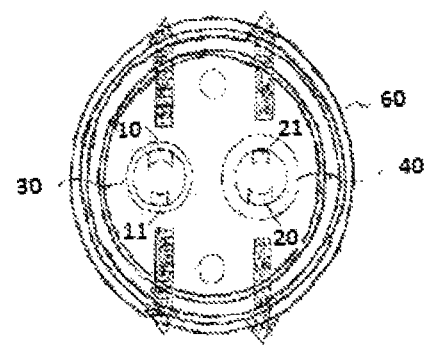
FIG. 3 shows a schematic top view of the arrangement of FIG. 1 with indicated flow directions for the blood and for the further fluid.
Figure 4:
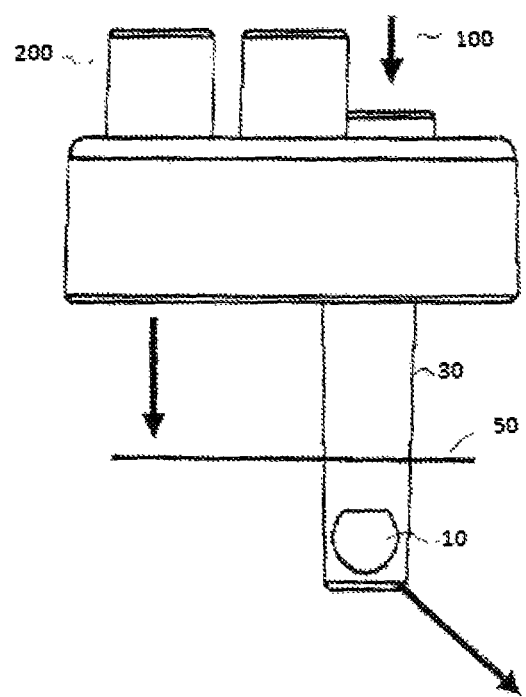
FIG. 4 shows a side view of a lid of a venous drip chamber from the prior art.

As can furthermore be taken from FIG. 3, the inlets are arranged such in the embodiment shown here that the inflow direction of the blood or of the further fluid is neither radial relative to the shell surface of the housing or of the lid of the chamber, which is cylindrical or circular in cross-section, nor tangential. Rather, it is provided here that the inflow direction of the blood or of the further fluid is effected in a direction which lies between the radial and the tangential direction. By means of this aspect of the present invention a better intermixing of the blood and of the infusion fluid is achieved and there is no turbulent effect which would lead to the level descending in the middle of the chamber and ascending at the sides thereof. Rather, it is achieved by the illustrated embodiment that the fluid level 50 or the surface of the fluid in the chamber remains largely flat, so that the vortex formation is largely or completely prevented, which in turn results in the fact that the occurrence of microbubbles or foam is prevented.

The venous drip chamber shown in FIGS. 1 to 3 with separate inlets for blood and the further fluid and with the special design of the inlets for blood and fluid at the tube section involves the advantage that neither a dripping of blood and/or the further solution onto the surface of the fluid or blood present in the chamber is effected as well as the further advantage that a vortex formation and hence a foam formation or a formation of microbubbles is largely or completely prevented. The one or more tube sections 30, 40 can be manufactured by the method of injection molding. In this method, providing the further openings 11, 21 involves certain advantages as regards the stability and the simplicity of the performance of the method. Thus, it is preferably provided that the lid or the headpiece 60 as a whole or at least the tube sections 30, 40 are manufactured by the method of injection molding.

The chamber of the present invention in particular is advantageously applicable in connection with the hemodiafiltration post-dilution treatment and preferably in connection with the online HDF post-dilution.

Thus, the supply port 200 preferably is a port for an infusion solution which is supplied to the blood after purifying the same in the dialyzer.

What is claimed is:

1. A drip chamber for a blood treatment system comprising:
   a chamber wall having a top;
   a space defined by the chamber wall;
   a circular lid connected to the chamber wall at the top of the chamber wall;
   at least one blood inlet; and
   at least one second inlet for a second fluid,
   wherein the at least one blood inlet and the at least one second inlet are connected with the at least one space,
   wherein both the at least one blood inlet and the at least one second inlet are formed on a first tube section and a second tube section, respectively, that protrude into the space of the chamber,
   wherein, in an operating condition of the chamber, the space of the chamber is at least partly filled up with blood or a mixture, the mixture comprising blood and either the second fluid or another fluid,
   wherein both the first tube section and the second tube section have a length such that the at least one blood inlet and the at least one second inlet are located below a blood level or a fluid level in the chamber,
   wherein the at least one blood inlet includes two blood inlets arranged on opposite sides of the first tube section and arranged so that an inflow of blood through the first tube section and into the space occurs in opposite respective directions, each of which directions lies between a radial direction and a tangential direction relative to the lid, and
   wherein the at least one second inlet includes two second inlets arranged on opposite sides of the second tube section and arranged so that an inflow of second fluid through the second tube section and into the space occurs in opposite directions, each of which directions lies between a radial direction and a tangential direction relative to the lid.

2. The chamber according to claim 1, wherein, in an operating condition, the space is at least partly filled up to a fluid level with blood or with a mixture of blood and the second fluid, an air cushion is disposed above the fluid level, each of the first and second tube sections extends downwardly from the lid, through the air cushion, and below the fluid level in the space, and the two blood inlets and the two second inlets are located below the fluid level in the space.

3. The chamber according to claim 1, wherein the space defined by the chamber wall has a vertical axis, and, in the operating condition, at least one of the first tube section and the second tube section extends parallel to the vertical axis or at an acute angle to the vertical axis.

4. The chamber according to claim 1, wherein, in an operating condition, the first tube section and the second tube section extend parallel or substantially parallel to each other.

5. The chamber according to claim 1, wherein the first tube section has a first length, and the second tube section has a second length that differs from the first length.

6. The chamber according to claim 1, wherein the first tube section comprises a first end wall, the second tube section comprises a second end wall, the two blood inlets are arranged adjacent to the first end wall, and the two second inlets are arranged adjacent to the second end wall.

7. The chamber according to claim 1, wherein the first tube section has a first longitudinal axis, the second tube section has a second longitudinal axis, the two blood inlets and the two second inlets are formed such that blood and the second fluid exit from the first and second tube sections, respectively, at angles in the range of from 30° to 150° relative to the first and second longitudinal axes, respectively.

8. The chamber according to claim 1, wherein the two blood inlets are arranged at the same vertical position along the first tube section and are of the same size.

9. A method of using a venous drip chamber in a blood treatment system, wherein the venous drip chamber comprises:
   a chamber wall having a top;
   a space defined by the chamber wall;
   a circular lid connected to the chamber wall at the top of the chamber wall;
   at least one blood inlet; and
   at least one second inlet for a second fluid,
   wherein the at least one blood inlet and the at least one second inlet are connected with the at least one space, wherein both the at least one blood inlet and the at least one second inlet are formed on a first tube section and a second tube section, respectively, that protrude into the space of the chamber, wherein, in an operating condition of the chamber, the space of the chamber is at least partly filled up with blood or a mixture, the mixture comprising blood and either the second fluid or another fluid, wherein both the first tube section and the second tube section have a length such that the at least one blood inlet and the at least one second inlet are located below a blood level or a fluid level in the chamber, wherein the at least one blood inlet includes two blood inlets arranged on opposite sides of the first tube section and arranged so that an inflow of blood through the first tube section and into the space occurs in opposite respective directions, each of which directions lies between a radial direction and a tangential direction relative to the lid, wherein the at least one second inlet includes two second inlets arranged on opposite sides of the second tube section and arranged so that an inflow of second fluid through the second tube section and into the space occurs in opposite directions, each of which directions lies between a radial direction and a tangential direction relative to the lid, wherein the first tube section comprises a blood supply port and the second tube section comprises an infusion fluid supply port, wherein an extracorporeal blood circuit containing blood is connected to the blood supply port, and wherein a supply of infusion fluid is in fluid communication with the infusion fluid supply port, the method comprising:

at least partly filling the space with the blood or with a mixture of the blood and the infusion fluid, up to a fluid level, to form an air cushion above the fluid level, wherein each of the first and second tube sections extends downwardly from the lid, through the air cushion, and below the fluid level in the space, and the two blood inlets and the two second inlets are located below the fluid level in the space.

10. The method according to claim 9, further comprising maintaining an air cushion above the fluid level.

11. The method according to claim 9, wherein the space defined by the chamber wall has a vertical axis, and at least one of the first and second tube sections extends parallel to the vertical axis or at an acute angle to the vertical axis.

12. The method according to claim 9, wherein the first tube section has a first longitudinal axis, the second tube section has a second longitudinal axis, the two blood inlets and the two second inlets are formed such that blood and the infusion fluid exit from the first and second tube sections, respectively, at angles in the range of from 30° to 150° relative to the first and second longitudinal axes, respectively.

13. The method according to claim 12, wherein the angles lie in the range of from between 60° and 120°.

14. The method according to claim 12, wherein the angles lie in the range of from between 80° and 100°.

15. The method according to claim 9, wherein the infusion fluid is an infusion solution comprising sodium chloride.

16. The method according to claim 9, wherein the infusion fluid is a dialysis solution.

\* \* \* \* \*